United States Patent [19]
Noriyuki et al.

[11] Patent Number: 5,030,726
[45] Date of Patent: Jul. 9, 1991

[54] POLYMERIZABLE CYCLIC UREA DERIVATIVES

[75] Inventors: Tsuboniwa Noriyuki, Higashiosaka; Urano Satoshi, Tsuzuki; Umemoto Hirotoshi, Uji; Sakamoto Hiroyuki, Nishinomiya; Tobinaga Kenshiro, Kawanishi; Tsuchiya Yasuyuki, Hirakata, all of Japan

[73] Assignee: Nippon Paint Co., Ltd., Osaka, Japan

[21] Appl. No.: 456,650

[22] Filed: Dec. 29, 1989

[30] Foreign Application Priority Data

Dec. 29, 1988 [JP] Japan ................................ 62-331996
Mar. 24, 1989 [JP] Japan ................................ 62-73134

[51] Int. Cl.$^5$ ................ C07D 243/04; C07D 239/36; C07D 245/02
[52] U.S. Cl. .................................... 540/460; 548/320; 544/316; 544/318; 528/245; 526/263; 525/402; 427/388.2
[58] Field of Search ................ 544/318, 315, 316; 548/320; 526/263; 427/388.2; 525/402; 528/245; 540/460

[56] References Cited

U.S. PATENT DOCUMENTS 4,104,220 8/1978 Sims ................................ 260/29.6 R
4,319,032 3/1982 Sanori ................................ 548/320
4,766,221 8/1988 Floyd ................................ 548/320
4,777,265 10/1988 Merger ................................ 548/320

FOREIGN PATENT DOCUMENTS 0078169 5/1983 European Pat. Off. .
0215245 3/1987 European Pat. Off. .

OTHER PUBLICATIONS

Journal of Organic Chemistry, vol. 29, No. 11, "Some Reactions of Ethylene Diisocyanate", Tilley et al., pp. 3347–3350.
Patent Abstracts of Japan, vol. 11, No. 133, Apr. 25, 1987, 61-271277-A.

*Primary Examiner*—Joseph L. Schofer
*Assistant Examiner*—Fred Zitomer
*Attorney, Agent, or Firm*—Wegner, Cantor, Mueller & Player

[57] ABSTRACT

The present invention relates to polymerizable cyclic urea derivatives which can be thermally split to give rise to an isocyanate group; and to a polymer having cyclic urea pendant groups, which can be cured by heating without any additional curing agent such as an isocyanate blocked with a volatile lower molecular weight material, so that volatile material is not released in a thermal curing process.

11 Claims, No Drawings

POLYMERIZABLE CYCLIC UREA DERIVATIVES

BACKGROUND OF THE INVENTION

The present invention relates to polymerizable cyclic urea derivatives and polymers having a pendant urea group.

The following cyclic urea (A):

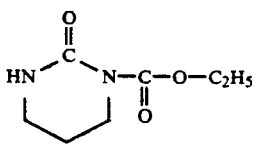

is reported by James N. Tilley in J. Org. Chem. 29 (11), 3347-50(1964), and thermocurable resinous compositions containing variations of (A) in the ester group have been also reported in the Japanese Patent Publication No. 24007/1988. Both prior references, however, do not refer to any polymerizable cyclic urea derivatives.

SUMMARY OF THE INVENTION

The present invention provides polymerizable cyclic urea derivatives represented by the following formula (I):

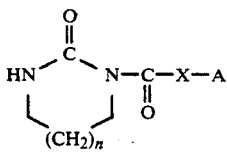

wherein n is 0 or an integer of 1-4, A is a $C_2$-$C_{18}$ alkynyl group, a $C_{18}$-$C_{18}$ alkynylaryl group or a formula:

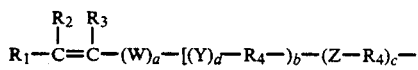

($R_1$, $R_2$ and $R_3$ are independently a hydrogen atom, a $C_1$-$C_5$ alkyl group or a phenyl group, $R_4$ is a straight or branched $C_1$-$C_9$ alkylene group, which may be the same or different, W is

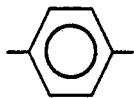

or —CO—, Y is an oxygen atom, a sulfur atom or —$NR_5$—($R_5$ is a hydrogen atom or a $C_1$-$C_5$ alkyl group), Z is —O—CO—, —NH—CO— or —S—CO—, a and d are independently 0 or 1, and b and c are independently an integer of 0–10], and X is an oxygen atom, a sulfur atom or —$NR_6$— [$R_6$ is a hydrogen atom or a $C_1$-$C_5$ alkyl group], and polymers having a corresponding cyclic urea pendant group.

These polymers are thermosetting because their cyclic urea pendant group may thermally decompose to give an isocyanate group which acts as a cross-linkable site. This decomposition does not generate any volatile lower molecular material which makes the invention different from a conventional lower isocyanate cross-linking agent which has been used in a coating composition. Accordingly, when such polymers are used as a vehicle resin for a thermocurable coating composition, there can be obtained a coat free from distortion attributed to vaporization of such a lower molecular decomposed material from a conventional isocyanate cross-linking agent.

THE DETAILED DESCRIPTION OF THE INVENTION

The present invention provides a polymerizable cyclic urea derivatives represented by the following formula (I):

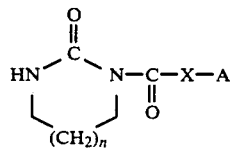

wherein n is 0 or an integer of 1-4, A is a $C_1$-$C_{18}$ alkynyl group, a $C_1$-$C_{18}$ alkynylaryl group or a formula:

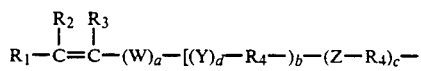

[$R_1$, $R_2$ and $R_3$ are independently a hydrogen atom, a $C_1$-$C_5$ alkyl group or a phenyl group, $R_4$ is a straight or branched $C_1$-$C_9$ alkylene group, which may be the same or different, W is

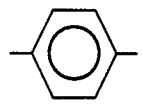

or —CO—, Y is an oxygen atom, a sulfur atom or —$NR_5$— ($R_5$ is a hydrogen atom or a $C_1$-$C_5$ alkyl group), Z is —O—CO—, —NH—CO— or —S—CO—, a and d are independently 0 or 1, and b and c are independently an integer of 0–10], and X is an oxygen atom, a sulfur atom or —$NR_6$-[$R_6$ is a hydrogen atom or a $C_1$-$C_5$ alkyl group], and polymers having a corresponding cyclic urea pendant group.

The polymerizable cyclic urea derivatives (I) according to the present invention can be obtained by reacting a compound represented by the formula (II):

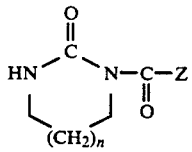

wherein Z is a halogen atom, a $C_1$-$C_{15}$ alkoxy group, an aryloxy group or an aralkyloxy group, and n is the same as aforementioned, with a compound represented by the formula (III):

A—X—H    (III)

wherein A and X are the same as the above, to replace the Z with the A—X.

The compound (II) can be obtained by reacting a cyclic urea with phosgene itself or a phosgene/alcohol reaction product according to the following reaction formula:

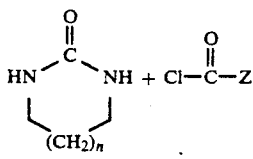

wherein n and Z are the same as aforementioned respectively.

The compound (III) has a hydrogen atom directly bonded to a oxygen, sulfur or nitrogen atom, that is, an active hydrogen atom. Such an active hydrogen atom containing compound (III) includes, for instance, (meta)acrylates such as 2-hydroxyethyl (meta)acrylate, 2-(2-hydroxyethoxy)ethyl (meta)acrylate, 4-hydroxybutyl (meta)acrylate, 3-hydroxypropyl (meta)acrylate, FM-1-5 ® available from Daicel Kagaku Kogyo K.K. and the like; (meta)acrylamides such as N-(2-hydroxyethyl) (meta)acrylamide, N-(2-hydroxypropyl) (meta)acrylamide, N-(hydroxymethyl) (meta)acrylamide and the like; styrenes such as 4-hydroxyethyl styrene, 4-hydroxy styrene and the like; polymerizable alcohols such as allyl alcohol, propargyl alcohol, cinnamyl alcohol and the like; an amino group-containing compound such as p-aminostyrene, p-vinylbenzylamine, p-vinylbenzylethylamine, p-(2-aminoethyl)styrene, vinylethylamine, vinylbutylamine, N-(3-methylaminopropyl)methacrylamide and the like; a sulfur containing compound such as allylthiols and the like.

The polymerizable cyclic urea derivatives of the present invention may be obtained by replacing Z of the compound (II) with A-X. This replacement may be effected at usually 0°-200° C., preferably about 50°-100° C. in a suitable solvent in the presence of a catalyst such as tin or basic catalysts, if necessary or without the same. A suitable solvent is one having no active hydrogen atom, for instance, hydrocarbons, halogenated hydrocarbon, ethers, esters and the like. A preferable example of such a solvent includes aliphatic hydrocarbons such as pentane, hexane, heptane, and the like; aromatic hydrocarbons such as benzene, toluene, xylene and the like; alicyclic hydrocarbons such as cyclohexane, methylcyclohexane, decalin and the like; petroleums such as naphtha, ligroin and the like; halogenated hydrocarbons such as carbon tetrachloride, chloroform, 1,2-dichloroethane and the like; ethers such as ethyl ether, isopropyl ether, anisole, dioxane, tetrahydrofuran and the like; ketones such as methyl ethyl ketone, methyl isobutyl ketone, cyclohexanone, acetophenone, isophorone and the like; esters such as ethyl acetate, butyl acetate and the like; acetonitrile, dimethylformamide, dimethyl sulfoxide or as such. These solvent may be used singly or as a mixture. A polymerization inhibitor may be used in the reaction, if necessary, but is not indispensable.

Further, the present invention provides new polymers having a pendant cyclic urea group represented by the formula (VI):

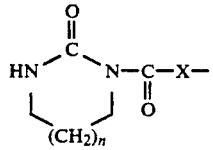 (IV)

wherein X and n are the same as aforementioned respectively, on the C—C backbone chain. The pendant group may be contained preferably in the amount of 0.1–88% by weight, more preferably 5 to 50% by weight based on the polymer weight. The molecular weight of the polymer excepting the pendant group may be preferably 500–100,000, more preferably 1,000–50,000.

The polymer can be obtained by homopolymerization or copolymerization of the aforementioned polymerizable cyclic urea derivatives. The copolymerization may be achieved between or among different monomers having the cyclic urea pendant group or the same with other monomers having no such cyclic urea pendant group. The copolymers may be random copolymers or block copolymers such as those obtainable by polymerizing oligomers of the monomers having no cyclic urea pendant group with monomers having a cyclic urea pendant group.

Examples of monomers copolymerizable with monomers having a cyclic urea pendant group include monoolefins and diolefins such as styrene, α-methylstyrene, α-ethylstyrene, 2-methyl-1-butene, ethylene, propylene, butylene, amylene, hexylene, butadiene-1,3, isoprene, and the like; halogenated monoolefins or diolefins such as α-chlorostyrene, chlorostyrene, α-bromostyrene and the like; organic or inorganic esters such as vinyl acetate, vinyl propionate, vinyl butyrate, vinyl benzoate, methyl methacrylate, ethyl methacrylate, propyl methacrylate, hexyl methacrylate, methyl acrylate, ethyl acrylate, propyl acrylate, methyl acetate, allyl chloride, allyl cyanamide, allyl acetate, allyl propyonate, allyl butyrate, dimethyl maleate, diethyl maleate, dimethyl fumarate, diethyl fumarate, dimethacryl fumarate, diethyl glutaconate and the like; organic nitriles such as acrylonitrile, methacrylonitrile, ethacrylonitrile, 3-octenenitile, crotonnitrile, oleonitrile, and the like; unsaturated carboxylic acids such as acrylic acid, methacrylic acid, crotonic acid, and the like; unsaturated alcohols such as monoester of unsaturated carboxylic acids as aforementioned with glycols such as ethylene glycol, propylene glycols and the like; unsaturated amides such as acrylamide, methacrylamide, crotonamide, and the like; unsaturated sulfonic acids or salts thereof such as 2-sulfoethyl acrylate, p-vinylbenzenesulfonic acid and the like.

The polymerization may be effected by radical polymerization of monomers aforementioned in an inert solvent in the presence of a polymerization initiator. As the polymerization initiator there are exemplified 2,2'-azobisisobutyronitrile, benzoyl peroxides, cumene hydroperoxide, tetramethylthiuram disulfide, 2,2'-azobis(4-methoxy-2,4-dimethylvaleronitrile), acetyl cyclohexylsulfonylperoxide, 2,2'-azobis(2,4-dimethylvaleronitrile) and the like. The polymerization initiator may be used in the amount of about 0.1–10% by weight based on the total amount of monomers to be polymerized. The preferable polymerization temperature is about 20°–200°C., more preferably 80°–150° C. The inert solvent includes, for instance, hydrocarbons, halogenated hydrocarbons, ethers, ester, alcohols, and the like; a preferable one includes aliphatic hydrocarbons such as hexane, heptane, and the like; aromatic hydrocarbons such as benzene, toluene, xylene and the like; alicyclic hydrocarbons such as cyclohexane, methylcyclohexane, decalin and the like; petroleum distillates such as petroleum ether, ligroin and the like; halogenated hydrocarbons such as carbon tetrachloride, chloroform, 1, 2-dichloroethane, and the like; ethers such as isopropyl ether, anisole, dioxane, tetrahydrofuran and the like; ketones such as acetone, methyl ethyl ketone, methyl isobutyl ketone, cyclohexanone, acetophenone, isophorone and the like; esters such as ethyl acetate, butyl acetate and the like; alcohols or glycols such as butanol, isopropanol, butyl cellosolve, ethylene glycol monophenyl ether, and the like, and others such as acetonitrile, dimethylformamide, dimethyl sulfoxide and the like. These solvents may be used as mixed.

The manner of the polymerization itself is not restricted, and may be carried out in the presence of other additives such as polymerization controlling agents.

The polymers of the present invention may be prepared by other methods, for instance, by reacting polymers previously obtained from the monomer (III):

A—X—H    (III)

(A and X are the same as defined above respectively) alone or with other monomers which are polymerizable with the monomer (III) with the compound (II):

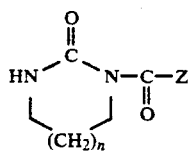

(II)

(n and Z are defined as above to the above respectively). The polymerization condition or monomers to be copolymerized may be the same as the aforementioned. The reaction condition introducing a cyclic urea pendant group into the polymer may be the same as the aforementioned in the preparation of polymerizable cyclic urea derivatives.

The polymerizable cyclic urea derivatives of the present invention can give rise to an isocyanate group by heating as illustrated below:

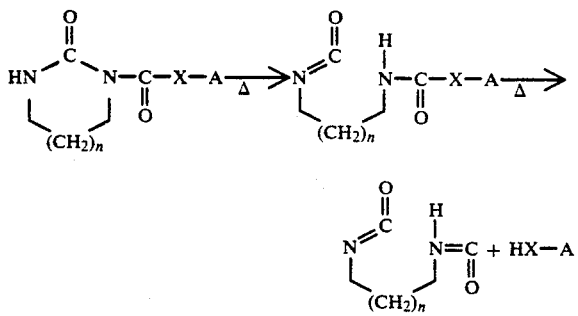

The reaction product is further decomposed by heating to give a compound having two isocyanate groups.

A polymer having cyclic urea pendant groups therein also gives rise to isocyanate groups by heating. A polyisocyanate can be used as a cross-linking agent as well known. Therefore, the cylic urea pendant group in the polymer of the present invention acts as a potentially cross-linkable group. That is, the polymer of the present invention can be called as a thermosetting polymer having potentially cross-linkable portions. As the polymer of the present invention does not give rise to a volatile lower molecular material in a cross-linking process, which is different from a conventional manner in which a polyisocyanate blocked with a lower molecular material is separately used, an excellent coat free from distortion such as shrinking attributed to volatilization of a lower molecular material at curing can be obtained. Therefore, the cyclic urea derivatives of the present invention are useful as a raw material for monomers, and the polymer having cyclic urea pendant groups is also very useful as a vehicle for coating composition. Further, the cyclic urea derivatives or the polymer having cyclic urea pendant groups of the present invention are also useful for an intermediate of other compounds, pharmaceuticals, or production thereof.

The present invention is illustrated by the following Examples, but it should not be construed that the present invention limitative to these Examples.

EXAMPLE 1

Preparation of 2-methacroyloxyethyloxy-carbonylpropyleneurea

Phenoxycarbonylpropyleneurea 100 g (450 mmol) and hydroxyethyl methacrylate 59 g (450 mmol) were dissolved in dioxane (900 ml) at 85°–90° C. Into the solution obtained was added dibutyltin dilaurate 400 mg, and the mixture was heated at 85°–90° C. with stirring for 13 hours. After the reaction, the solution was concentrated, and the obtained crude product was treated with ether to give a precipitate of 90 g (yield: 77.5%) as the title compound, which was analyzed and showed:

NMR: 6.39, 6.14(t), 5.60(t), 4.48(m), 4.40(m), 3.76(t), 3.32(dt), 1.98(m), 1.93(s),
IR: 3350, 1770, 1720, 1679, 1640,
mp: 66°–68° C.
appearance: colorless prism.

EXAMPLE 2

Preparation of 2-(p-vinylphenyl)ethyloxycarbonylpropyleneurea

Phenoxycarbonylpropyleneurea 8.2 g (37.3 mmol) and hydroxyethylstyrene 5 g (37.3 mmol) were dissolved into dioxane 90 ml by heating. Into the solution obtained was added dibutyltin dilaurate 0.5 g, and the mixture was heated for 6 hours with stirring. After the reaction the solution was concentrated to give a solid mass, which was then purified by column chromatography. The title compound 3.9 g (yield: 40%) was obtained, which was analyzed to:

NMR: 7.36(m), 7.23(m), 6.73(dd), 6.68(dd), 6.70 (dd), 6.65 (dd), 5.83, 5.74 (dd), 5.69(dd), 5.23(dd), 5.20(dd),
IR: 3260, 1780, 1710, 1610,
mp: 117°–119° C.

EXAMPLES 3–7

The polymerizable cyclic urea derivatives were prepared as generally described in Example 1, with the exception that the ingredients as shown in Table 1 were employed. The obtained products were identified by NMR and IR sectrum and yields are shown in Table 1.

TABLE 1

| Ex. No. | Compound (III) | Phenoxycarbonyl propyleneurea | Dioxane (ml) | Dibutyltin dilaurate (g) | Product | Yield |
|---|---|---|---|---|---|---|
| 3 | 2-hydroxyethylacrylate | 8.2 g | 90 | 0.5 | Acryloyloxyethyloxy- | 3.61 g |

TABLE 1-continued

| Ex. No. | Compound (III) | Phenoxycarbonyl propyleneurea | Dioxane (ml) | Dibutyltin dilaurate (g) | Product | Yield |
|---|---|---|---|---|---|---|
| 4 | FM-2*1 4.32 g, 37.3 mmol 13.4 g, 37.3 mmol | 37.3 mmol 8.2 g 37.3 mmol | 100 | 0.5 | carbonylpropyleneurea FM-2-PU*2 | 40% 9.0 g 50% |
| 5 | Allylalcohol 2.16 g, 37.3 mmol | 8.2 g 37.3 mmol | 90 | 0.5 | Allyloxycarbonyl- propyleneurea | 3.1 g 45% |
| 6 | Propargyl alcohol 2.1 g, 37.3 mmol | 8.2 g 37.3 mmol | 90 | 0.5 | Propargyloxycarbonyl- propyleneurea | 3.5 g 52% |
| 7 | Cinnamyl alcohol 5.0 g, 37.3 mmol | 8.2 g 37.3 mmol | 150 | 0.5 | 3-phenyl-2-propene- oxycarbonylpropyleneurea | 1.9 g 20% |

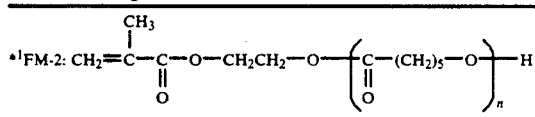

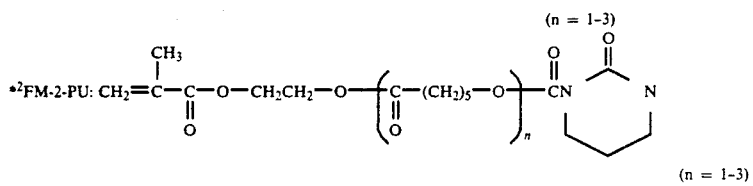

EXAMPLE 8

Preparation of homopolymer of 2-methacryloyloxyethyloxylcarbonylpropyleneurea:

2-Methacryloyloxyethyloxycarbonylpropyleneurea 5 g was dissolved into dimethylformamide 5 g, into which a polymerization initiator, t-butylperoxy-2-ethylhexanoate 50 mg was added. The mixture obtained was heated at 100° C. over 3 hours to give the title polymer (viscosity: 5.4 cp at 25° C. (EL type viscometer)).

EXAMPLE 9

Preparation of copolymer of 2-methacryloyloxyethyloxycarbonylpropyleneurea:

2-methacryloyloxyethyloxycarbonylpropyleneurea (50 g) and 2-ethylhexyl acrylate 150 g were heated together with dioxane 400 g at 80°-85° C. to give a solution, into which a solution of azobisisobutyronitrile 4.8 g in dioxane 200 g was added dropwise over 1.5 hours. The mixture was kept at the same temperature for two hours to give the title compound having a molecular weight ($\overline{Mn}$) of 2670.

EXAMPLES 10-16

According to the Example 9 but with some variations indicated in Table 2 seven kinds of copolymer were prepared. A molecular weight of each copolymer obtained as well as the variations in the polymerization are shown in Table 2, in which the abbreviations mean the following:

MCPU: 2-methacryloyloxyethyloxycarbonylpropyleneurea,

2EHA: 2-ethylhexyl acrylate,

FM-2®  (available from Daicel Kagaku Kogyo K.K.): $CH_2=CCH_3COOCH_2CH_2O(CO(CH_2)_5-O)_n-H$, (n=1-3)

NKM-20G® (available from Shin Nakamura Kagaku K.K.): $CH_2=CCH_3COOC_2H_4OC_2H_4OCH_3$,

HEMA: $CH_2=CCH_3COOCH_2CH_2OH$,

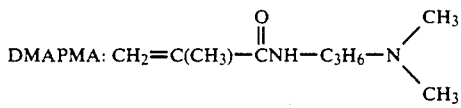

St: styrene,
n-BA: butyl acrylate,
AIBN: azobisisobutyronitrile,

TABLE 2

| Ex | MCPU | 2EHA | FM-2 | NKM20G | HEMA | DMAPMA | St | n-BA | AIBN |
|---|---|---|---|---|---|---|---|---|---|
| 10 | 2.0 g | 7.5 g | — | — | 0.5 g | — | — | — | 0.3 g |
| 11 | 2.0 g | 5.5 g | 0.5 g | — | — | — | 2.0 g | — | 0.3 + 0.2 g |
| 12 | 2.0 g | 6.0 g | 1.0 g | — | — | — | 1.0 g | — | 0.3 + 0.2 g |
| 13 | 2.0 g | 6.0 g | — | — | — | 0.5 g | — | 1.5 g | 0.3 + 0.1 g |
| 14 | 2.5 g | 5.0 g | 0.5 g | — | — | — | 2.0 g | — | 0.3 + 0.1 g |
| 15 | 2.5 g | — | — | — | — | — | 7.5 g | — | 0.3 + 0.3 g |
| 16 | 2.5 g | 2.5 g | — | 2.5 g | — | — | 2.5 g | 2.5 g | 0.3 + 0.2 g |

| Ex | dioxane | temperature | time | CONV. | viscosity | molecular weight Mn |
|---|---|---|---|---|---|---|
| 10 | 30 g | 80° C. | 1.5 h | 106% | 33 | 2700 |
| 11 | 30 + 2 g | 80° C. | 5 h | 100% | 10.2 | 3500 |
| 12 | 30 + 2 g | 80° C. | 5 h | 101% | 13.4 | 2800 |
| 13 | 30 + 1 g | 80° C. | 3 h | 102% | 28.5 | 1400 |
| 14 | 30 + 1 g | 80° C. | 4 h | 105% | 12.3 | — |
| 15 | 30 + 3 g | 80° C. | 8 h | 101% | 16.8 | 3900 |
| 16 | 37.5 g | 80° C. | 7 h | 102% | 16.8 | 4400 |

EXAMPLE 17

Preparation of 2-(p-vinylphenyl)ethyloxycarbonylpropyleneurea homopolymer:

2-(p-Vinylphenyl)ethyloxycarbonylpropyleneurea 0.5 g was dissolved in dimethylformamide 1.5 g, into which an initiator, AIBN 60 mg was then added. The mixture was heated at 75°-80° C. for 7 hours to give the title homopolymer (viscosity: 3.5 cp at 25° C. (EL type)).

EXAMPLE 18

Preparation of 2-(p-vinylphenyl)ethyloxycarbonylpropyleneurea copolymer:

2-(p-Vinylphenyl)ethyloxycarbonylpropyleneurea 0.5 g, n-butylacrylate 1.5 g and dioxane 5.5 g was mixed, and heated at 75°–80° C. Into the solution obtained was added AIBN 60 mg and the reaction was continued to give the title copolymer (viscosity: 27.5 cp at 25° C. (EL type)).

EXAMPLE 19

Preparation of 2-(p-vinylphenyl)ethyloxycarbonylpropyleneurea copolymer:

Mixture of 2-(p-vinylphenyl)ethyloxycarbonylpropyleneurea 0.5 g, 2-ethylhexylacrylate 1.4 g and FM-2 ® (available from Daicel Kagaku Kogyo K.K.) 0.1 g and dioxan 4.5 g was dissolved by heating at 75°–80° C., into which AIBN 60 mg was added, and reacted for 7 hours to give the title copolymer having a viscosity of 20.2 cp at 25° C. (EL type).

EXAMPLE 20

Preparation of 2-methacryloyloxyethyloxycarbonylpropyleneurea

2-Methacryloyloxyethyloxycarbonylpropyleneurea 40 g and styrene 60 g were dissolved in dimethylformamide to form a solution having a nonvolatile content of 40% by weight. Into the solution were added methyl styrene dimer 10 g and AIBN 5.5 g and polymerized at 80° C. for 8 hours to obtain the title copolymer having a number average molecular weight of 1,800 (conversion rate: 92.6%)

EXAMPLE 21–30

Copolymers were prepared as generally described in Example 20, with the exception that monomers and polymerization conditions described in Table 3 were employed.

TABLE 3

| Ex. No. | Monomers and chain transfer agnet (weight ratio) | AIBN (g) | Reaction temp. (°C.) | Reaction time (hr) | Conversion rate (%) | Molecular weight (Mn) |
|---|---|---|---|---|---|---|
| 21 | St/MCPU = 60/40 | 5.5 | 80 | 8 | 93 | 5000 |
| 22 | St/MCPU = 60/40 (10) | 5.5 | 80 | 8 | 93 | 1800 |
| 23 | St/EHA/MCPU = 40/20/40 | 5.5 | 80 | 8 | 90 | 2300 |
| 24 | DMAPMA/NK-20/MCPU(MSD) = 20/40/40 (10) | 5.5 | 80 | 8 | 85 | 800 |
| 25 | DMAPMA/St/MCPU(MSD) = 20/40/40 (10) | 5.5 | 80 | 8 | 77 | 800 |
| 26 | DMAPMA/St/MCPU = 20/40/40 | 5.5 | 80 | 8 | 97.2 | 1100 |
| 27 | St/EHA/MAA/MCPU(MSD) = 40/20/2.4/40 (10) | 5.5 | 80 | 8 | 70 | 600 |
| 28 | St/EHA/MAAm/MCPU(MSD) = 40/20/10/40 (10) | 5.5 | 80 | 8 | 70 | — |
| 29 | St/EHA/AN/MCPU(MSD) = 40/20/10/40 (10) | 5.5 | 80 | 8 | 70 | 900 |
| 30 | MCPU = 100 | 5.5 | 80 | 8 | 100 | 500 1200 |

MAA: Methacrylic acid
AN: Acrylonitrile
MAAM: Methacrylamide
MSD: α-methylstyrene dimer
EHA: 2-Ethylhexyl acrylate

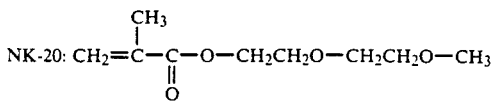

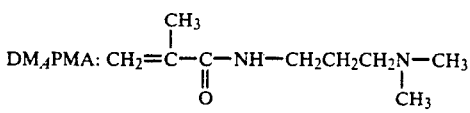

What is claimed is:

1. Polymerizable cyclic urea derivatives represented by the following formula (I):

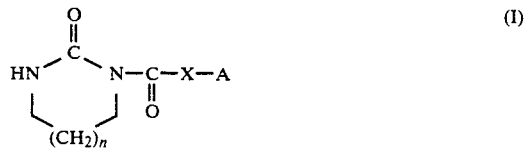

wherein n is 0 or an integer of 1–4, A is a $C_2$-$C_{18}$ alkynyl group, a $C_8$-$C_{18}$ alkynylaryl group or a group of the formula:

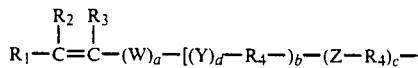

wherein $R_1$, $R_2$ and $R_3$ are independently a hydrogen atom, a $C_1$-$C_5$ alkyl group or a phenyl group, $R_4$ is a straight or branched $C_1$-$C_9$ alkylene group, which may be the same or different, W is

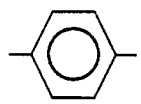

or —CO—, Y is an oxygen atom, a sulfur atom or —$NR_5$— wherein $R_5$ is a hydrogen atom or a $C_1$-$C_5$ alkyl group, Z is —O—CO—, —NH—CO— or —S—CO—, a and d are independently 0 or 1, and b and c are independently an integer of 0–10, and X is an oxygen atom, a sulfur atom or —$NR_6$— wherein $R_6$ is a $C_1$-$C_5$ alkyl group.

2. Polymerizable cyclic urea derivatives of claim 1, in which $R_2$ is a hydrogen atom, W is

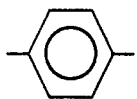

or —CO—, and a is 0 or 1.

3. Polymerizable cyclic urea derivatives of claim 1, in which $R_1$, $R_2$ and $R_3$ are hydrogen atoms, W is —CO— and a is 1.

4. Polymerizable cyclic urea derivatives of claim 1, in which $R_1$ and $R_2$ are hydrogen atoms, $R_3$ is methyl, W is —CO— a is 1.

5. Polymerizable cyclic urea derivatives of claim 1, in which $R_1$, $R_2$ and $R_3$ are hydrogen atoms, W is

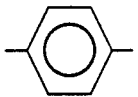

and a is 1.

6. Polymerizable cyclic urea derivatives of claim 1, in which $R_1$ and $R_3$ hydrogen atoms, $R_2$ is phenyl, W is —CO— and a is 1.

7. Polymerizable cyclic urea derivatives of claim 1, in which $R_1$, $R_2$ and $R_3$ are hydrogen atoms and a is 0.

8. Polymerizable cyclic urea derivatives of claim 1, in which A is selected from an acryloyl, methacryloyl, crotonoyl, vinyphenyl, cinnamoyl, propioloyl and propargyl group.

9. Polymerizable cyclic urea derivatives of claim 1, wherein X is an oxygen atom.

10. Polymerizable cyclic urea derivatives of claim 2, wherein X is an oxygen atom.

11. Polymerizable cyclic urea derivatives of claim 4, wherein X is an oxygen atom.

* * * * *